United States Patent [19]
Gordon

[11] Patent Number: 4,569,836
[45] Date of Patent: Feb. 11, 1986

[54] CANCER TREATMENT BY INTRACELLULAR HYPERTHERMIA

[76] Inventor: Robert T. Gordon, 4936 W. Estes, Skokie, Ill. 60076

[21] Appl. No.: 497,704

[22] Filed: May 24, 1983

Related U.S. Application Data

[63] Continuation of Ser. No. 296,575, Aug. 27, 1981, and Ser. No. 936,577, Aug. 22, 1978.

[51] Int. Cl.⁴ .................... A61K 43/00; A61K 49/00; A61F 7/00; A61N 5/12
[52] U.S. Cl. .................................... 424/1.1; 128/1 R; 128/1.1; 128/399; 128/205.26; 128/804; 424/9
[58] Field of Search ............... 424/1.1, 9; 128/804, 128/1 R, 1.1, 659, 399, 205.26

[56] References Cited

U.S. PATENT DOCUMENTS

| | | | |
|---|---|---|---|
| 3,663,685 | 5/1972 | Evans | 424/1.1 |
| 3,663,686 | 5/1972 | Grotenhuis et al. | 424/1.1 |
| 3,663,687 | 5/1972 | Evans | 424/1.1 |
| 3,991,770 | 11/1976 | Le Veen | 128/804 |
| 4,106,488 | 8/1978 | Gordon | 128/1 R |
| 4,136,683 | 1/1979 | Gordon | 128/1.3 |
| 4,202,323 | 5/1980 | Zweig et al. | 424/1.1 |
| 4,303,636 | 12/1981 | Gordon | 424/1.1 |
| 4,323,056 | 4/1982 | Borrelli | 128/804 |
| 4,335,044 | 4/1982 | Mosbach | 424/1.1 |
| 4,337,760 | 7/1982 | Rubin | 128/804 |
| 4,357,259 | 11/1982 | Senyei et al. | 424/1.1 |
| 4,359,453 | 11/1982 | Gordon | 424/1.1 |
| 4,363,793 | 12/1982 | Blau et al. | 424/1.1 |

OTHER PUBLICATIONS

Cavaliere et al., Cancer, 20(8), 1351-1381 (1967).
Wildermuth, J.A.M.A., 3/22/65, vol. 191, No. 12, pp. 114-118.
R. T. Gordon, J. R. Hines, and D. Gordon-Intracellular Hyperthermia-A Biophysical Approach to Cancer Treatment Via Intracellular Temperature and Biophysical Alterations-1979-pp. 83-102, Medical Hypotheses 5.
Robert Thomas Gordon, James R. Hines and David Gordon-Intracellular Hyperthermia: Selective Cancer Cell Destruction by the Biophysical Alteration of Intracellular Properties-1978-pp. 425-426, IRCS Medical Science: Biomedical Technology; Cancer; Cell and Membrane Biology 6.

*Primary Examiner*—Christine M. Nucker
*Attorney, Agent, or Firm*—Lalos, Keegan, Marsh, Bentzen & Kaye

[57] ABSTRACT

A treatment of cancer by the application of chemical reactions intracellularly capable of the intracellular generation of heat so as to induce selective thermal death of cancer cells in living tissue. Metabolizable minute particles of a size less than one micron are intravenously injected into the patient and absorbed by the cancer cells. The oxygen level of the patient's blood is then increased. The rate of intracellular chemical reaction in the cancer cells due at least in part to the intracellular presence of these minute particles is thereby increased and intracellular heat generated. The oxygen level is increased until the intracellular temperature has increased at least 8.0 degrees Centigrade but not more than 9.5 degrees Centigrade thereby selectively killing the cancer cells without damaging the normal cells.

30 Claims, No Drawings

CANCER TREATMENT BY INTRACELLULAR HYPERTHERMIA

This is a continuation of application Ser. No. 936,577, filed Aug. 22, 1978 & Ser. No. 296,575 filed Aug. 27, 1981.

INTRODUCTION

This invention relates generally to a process and composition for the treatment of cancer in living tissues. More particularly, the present invention relates to method and composition for the treatment of cancer by intracellularly killing the cancer cells without injuring the normal cells.

BACKGROUND OF THE INVENTION

There are presently a number of methods and techniques for the treatment of cancer, among which may be included: radiation therapy, chemotherapy, immunotherapy, and surgery. The common characteristic for all of these techniques as well as most other presently known techniques is that they are extracellular in scope, that is, the cancer cell is attacked and attempted to be killed through application of the killing force or medium outside of the cell.

The extracellular approach is found to be less effective and efficient because of the difficulties of penetrating the tough outer membrane of the cancer cell that is composed of two protein layers with a lipid layer in between. Of even greater significance is that to overcome the protection afforded the cell by the cell membrane in any extracellular technique, the attack on the cancer cells must be of such intesity that considerable damage is caused to the normal cells resulting in severe side effects upon the patient. These side effects have been found to limit considerably the effectiveness and usefulness of these treatments.

A safe and effective cancer treatment has been the goal of investigators for a substantial period of time. Such a technique, to be successful in the destruction of the cancer cells, must be selective in effect upon the cancer cells and produce no irreversible damage to the normal cells. In sum, cancer treatment must selectively differentiate cancer cells from normal cells and must selectively weaken or kill the cancer cells without affecting the normal cells as described in U.S. Pat. No. 4,106,488.

It has been known that there are certain physical differences that exist between cancer cells and normal cells. One primary physical difference that exists is in the temperature differential characteristics between the cancer cells and the normal cells. Cancer cells, because of their higher rates of metabolism, have higher resting temperatures compared to normal cells. In the living cell, the normal temperature of the cancer cell is known to be 37.5° Centigrade, while that of the normal cell is 37° Centigrade. Another physical characteristic that differentiates the cancer cells from the normal cells is that cancer cells die at lower temperatures than do normal cells. The temperature at which a normal cell will be killed and thereby irreversibly will be unable to perform normal cell functions is a temperature of 46.5° Centigrade, on the average. The cancer cell, in contrast, will be killed at the lower temperature of 45.5° Centigrade. The temperature elevation increment necessary to cause death in the cancer cell is determined to be at least approximately 8.0° Centigrade, while the normal cell can withstand a temperature increase of at least 9.5° Centigrade.

It is known, therefore, that with a given precisely controlled increment of heat, the cancer cells can be selectively destroyed before the death of the normal cells. On the basis of this known differential in temperature characteristics, a number of extracellular attempts have been made to treat cancer by heating the cancer cells in the body. This concept of treatment is referred to as hyperthermia. To achieve these higher temperatures in the cancer cells, researchers have attempted a number of methods including inducing high fevers, utilizing hot baths, diathermy, applying hot wax, and even the implantation of various heating devices in the area of the cancer.

At this time, none of the extracellular approaches to treat cancer have been truly effective and all have the common characteristic of approaching the problem by treating the cancer cell extracellularly. The outer membrane of the cancer cell, being composed of lipids and proteins, is a poor thermal conductor, thus making it difficult for the application of heat by external means to penetrate into the interior of the cell where the intracellular temperature must be raised to effect the death of the cell. If, through the extracellular approaches of the prior hyperthermia techniques, the temperatures were raised so high as to effect an adequate intracellular temperature to kill the cancer cells, many of the normal cells adjacent to the application of heat could very well be destroyed.

OBJECT OF THE INVENTION

It is therefore the purpose and principal object of the present invention to kill the cancer cells selectively by intracellularly generating a temperature and by changing biophysical characteristics that will kill the cancer cells while producing no harmful effects upon the normal cells.

SUMMARY OF THE INVENTION

A treatment of cancer by the application of chemical reactions intracellularly capable of the intracellular generation of heat so as to induce selective thermal death of cancer cells in living tissue. This process allows for the selective treatment of cancer cells in living tissue without damaging the normal cells by the compartmentalized alteration of biophysical properties in the cancer cell.

The process comprises introducing minute particles into the interior of the cells of living tissue. These particles being injected intravenously while suspended in an appropriate solution are of a size generally having a diameter of approximately 1 micron or less and are of a material with properties which permit metabolism by the cell and an increased rate of metabolism or oxidation by the availability of an increased amount of oxygen. Introducing the particles as described, the patient is thereafter subjected to a hyperbaric oxygen chamber which raises the oxygen level of the blood and results in an increase of the metabolism or oxidation of the particles and an increase in the intracellular temperature. The patient is kept in the hyperbaric oxygen chamber sufficiently long to raise the temperature of the cells by an increment of 8.0°–9.5° Centigrade thus killing the cancer cells without harming the normal cells, since this increment is sufficient to kill the cancer cells but is not great enough to injure the normal cells. Generating the heat intracellularly instead of extracellularly results in the cell's membrane, which is an effective thermal barrier, enhancing the process by keeping the heat within the cells instead of outside of the cells.

The process is further enhanced by the phagocytic characteristic of the cancer cells which causes the particles to concentrate within the cancer cells and thus facilitate a greater generation of heat within the cancer cells. Further selectivity and increased affinity of the cancer cells for these particles may be achieved by incorporating specific radioisotopes or tumor specific antibodies bound to these particles.

2,3-Diphosphoglycerate (2,3 DPG) may be used to increase the availability of oxygen to the cells by producing a shift in the oxyhemoglobin curve. Similarly, the addition of phosphates to the patient may be utilized to increase the patient's level of 2,3 DPG and increase the availability of oxygen to the cells, thereby increasing intracellular metabolism. This technique may be used in combination with hyperbaric oxygenation.

These particles introduced intracellularly as described may be used in combination with a chemotherapeutic agent by having the chemotherapeutic agent encapsulated within said particles or integrated with said particles and after having been delivered to the interior of the cells, the application of the hyperbaric oxygen chamber and the resultant intracellular generation of heat would act to increase the efficacy of the chemotherapeutic agent.

The present invention further defines a novel cancer-treating composition which includes minute particles suspended in an aqueous solution in dosage form. These particles may be bound to radioisotopes or to cancer antibodies to more effectively direct the absorption by the cancer cells.

An alternate to the use of the hyperbaric oxygen chamber entails the use of two or more chemicals capable of intracellular absorption and capable of reacting with each other to produce heat, and introduced intravenously sequentially with a time period and dosage adjusted so as to generate intracellularly an increment of 8.0°-9.5° Centigrade.

DETAILED DESCRIPTION OF THE INVENTION

The present invention achieves a precise increment of heat rise within the cancer cell and within the cytoplasm. The thermal barrier that characteristically exists as the outer membrane or cell wall of the cell is now utilized as a means of retaining the heat produced within the cell, rather than, as in the past, preventing any heat build-up within the cell. On the basis of the cell resting temperatures and the temperature necessary to produce cell death, the increment that the cell temperature must be raised to cause the cell death is critical. For the normal cell, the temperature rise is 9.5° Centigrade, while in the cancer cell the temperature rise is approximately 8.0° Centigrade. Thus, any temperature rise in the cancer cell or in the normal cell that is at least 8.0° Centigrade and not more than 9.5° Centigrade above the normal cell temperature will result in a selective destructive of the cancer cell without any harmful effects to the normal cell.

In accordance with the present invention, there are found to be a number of approaches that can successfully achieve the end result of an intracellular heat rise and an intracellular destruction of the cancer cell.

In its simplest and broadest aspect, the present invention contemplates the introduction into the cancer cell of a minute particle of a material permitting metabolism by oxidation by the cells and then subjecting all the cells generally, including the normal cells, to an increased oxygen supply resulting from the increase in the oxygenation of the blood resulting from the application of the hyperbaric oxygen chamber and by the increase of levels of 2,3-Diphosphoglycerate.

This principle on which the present invention is based is also grounded upon the known fact that cancer cells have a far greater affinity for particles and for foreign substances such as these minute particles that are to be introduced, than do the normal cells. Due to this phagocytic characteristic of cancer cells, such particles tend to concentrate in significantly greater numbers within the cancer cells, as compared to the normal cells. Electron micrographs have been taken of tissue following the introduction of such particles and clearly illustrate the selective concentration of the particles in the cancer cells. This is expected due to the higher rate of metabolism of the cancer cells and because tumors develop neo-vascularization. The new capillaries and blood vessels formed in tumors have increased permeability to foreign particles when compared to the capillaries and the blood vessels of normal tissues.

The particles which are useful in accordance with the present invention, are those such as the dextran iron oxyhydroxide particles and other iron complexes used in the treatment of anemia which are readily metabolized and oxidized. Similarly, the compounds of gallium, indium, technetium, strontium, iodine, and other compounds compatible with living tissue may be useful. The particle size of the particles should not be greater than about 1 micron. Preferable particle size would be less than the 1 micron size.

The minute particles described are to be injected intravenously into the patient through the use of any suitable compatible liquid vehicles. Aqueous solutions of any such body-acceptable materials as dextran, dextrose, saline or blood, as well as water alone, can be used. The liquid vehicle should sustain the particles in suspension for the subsequent injection. Concentrations of such body-acceptable materials that may be useful are those that are up to about 50% by weight in water. Usually a solution of about 1% to 10% is adequate. The concentration of the particles in the solution is not critical and is usually in a range between 50 to 75 mg/cc of the solution.

The intravenous injection into the patient generally is in an amount such that between 1 to 10 mg. of the particles per kg of body weight of the patient are injected at one time; however, up to approximately 20–45 mg. total dosage per kg of body weight is possible. The greater weight of the patient, the higher the permissible dosage. The total amount of the dosage is not critical though 2 to 3 injections may be injected within a 24 to 72 hour period. The time span for the injections may vary greatly for various patients and for various objectives.

The minute particles contained in the aqueous medium are transported through the blood stream and have been found to be phagocytized by the cancerous cells to a far greater degree than, and in fact in some cases to the possible exclusion of, their admittance into the normal cells.

Electronmicrographs of the cancerous tissue have proven the selective pickup of these particles by the cancer cells.

The intracellular characteristics of the present technique are evident. It has been found that the intracellular temperature of the cells may be raised between 8.0° Centigrade and 9.5° Centigrade to cause death in the cancer cell without damage being caused to the normal cells.

The next stage of the present invention is to bring about intracellular heating by raising the rate of metabolism or oxidation of the dextran iron complex particle in the cell. The monitoring of the temperatures of the living cells is a presently available technique well-known to the medical science.

The increased increment of intracellular heating is achieved by application of a hyperbaric oxygen chamber which increases the oxygenation of the blood which increases the amount of oxygen available to the cells which have already absorbed the minute particle which is capable of using this additional oxygen to increase its rate of metabolism or oxidation. The use of a hyperbaric oxygen chamber with a pressure of several atmospheres is well-known to the medical science as a means of increasing the oxygenation of the blood. Similarly 2,3-Diphosphoglycerate may be used to increase the availability of oxygen to the cells in order to increase the intracellular metabolism.

The time necessary to generate intracellularly by these chemical means the increment of heat desired depends upon the dosage of particles absorbed and the pressure of the hyperbaric oxygen chamber. In general, it has been found that a period of approximately 1 to 2 hours in a hyperbaric oxygen chamber of 2 atmospheres pressure will bring about the desired increment of intracellular temperature increase.

The use of a hyperbaric oxygen chamber to increase the oxygenation of the blood and thereby the supply of oxygen to the cell will not, of itself, materially increase the rate of metabolism in the cell, but when the process is accompanied by the prior absorption within the cell of a "fuel" such as a material like iron oxyhydroxide which in the metabolic processes is oxidized to "ferritin" or a sugar complex which is oxidized, then the availability of an increased supply of oxygen (assisted by increased level of 2,3-Diphosphoglycerate) results in an accelerated chemical reaction and a greater intracellular generation of heat sufficient to raise the intracellular temperature.

EXAMPLE I

As a specific example of the simplest form of the present invention, iron oxyhydroxide particles of 0.7 micron size are suspended in a 5% dextrose aqueous solution in an amount of about 50 mg. of the particles per cc. Dosages in the amount of 30 mg. per kg. of body weight each of the particles should be made twice, by intravenous injections, each being 24 hours apart. The patient is then ready for the application of the hyperbaric oxygen chamber. A pressure of 2 atmospheres is maintained in the hyperbaric oxygen chamber (oxygen at normal pressure, hyperbaric air chamber, or any other conventional means of increasing oxygenation of blood may be used). Microprobes are used to constantly monitor temperatures in various parts of the body. Under these conditions, after about 1½ hours, the temperature within the cells will have increased by an increment of 8.5° Centigrade. At this temperature the cancer cells in the living tissue will have been killed while the normal cells will recover normal cellular functions. 2,3-Diphosphoglycerate levels are raised in the patient in order to facilitate the availability of oxygen to the cells. The 2,3-Diphosphoglycerate level is raised by the pretreatment injection of phosphates.

While the simplest aspect of the invention has been described in detail, the selectivity of the minute particles for the cancer cells may be increased through the use of several techniques.

The addition of a cancer cell seeking agent such as radioisotopes or a tumor specific antibody is useful in directing the minute particles more selectively to the cancer cells. It is known that both radioisotopes and tumor specific antibodies have an affinity for the cancer cells and it is for this reason that the radioisotopes and antibodies have been found to have some application in the treatment of certain tumors. It is also possible that the radioisotopes may be used to substitute for the minute particles and be injected intravenously so as to be selectively taken up by the cancerous cells. Many of these radioisotopes, whether chemically or physically combined with other particles or used alone, are capable of metabolism or oxidation and with an increased supply of oxygen would react so as to generate heat intracellularly and thus raise the temperature of the cancer cells to the destructive temperature. Typical examples of useful radioisotopes are such as gallium-67, indium-113m, technetium-99m, fluorine, selenium-75. A great many other radioisotopes are useful and the above are only examples. The size and concentration of the radioisotopes alone or attached to the minute particles and the manner of injection is precisely the same as previously described.

These radioisotopes or antibodies may be bound to the particles as iodine-131 (the radioisotopes) has been bound to albumin for lung scanning in the past. Antibodies, for instance, may be attached to the iron dextran or other minute particles by use of an intermediate reducing glucose unit or its derivative such as metasaccharinic acid, in a conventional manner and as described in Example III, much as high molecular weight dextran is bound to ferric hydroxide.

It is known that antibodies can be formed by injection of cancer cells removed from one patient with cancer and injected into another patient. The injection of the cancer cells will in turn form antibodies in the substitute host as a defense against the foreign tumor cells from the original donor. These antibodies can be then selectively isolated and in the past have been used to treat selected specific tumors. These antibodies have usefulness in the present invention as a selective cancer cell seeking agent.

These antibodies may be bound chemically or physically to the minute particles and then re-injected into the patient to be treated. Due to the antibodies' specificity for the original tumor cells, the antibodies bound to the particles will even more selectively induce the particles to be phagocytized by the cancer cells.

Antibodies with radioactive isotopes may be produced by feeding the animals producing the antibodies, labeled amino acids. This labeled amino acid is then incorporated into the antibody.

Large chemical entities can be attached to antibody molecules. Large proteins may be attached via diagotized atoxyl (P-amino-benzene arsenic acid). Antibodies may be bound while they are attached to a hapten or to an antigen. This protects the immunologically specific site of the antibody during the binding procedure.

It should be understood that the entire purpose of selective direction of the particles or the radioisotopes is that the application of a hyperbaric oxygen chamber (with elevation of 2,3-Diphosophoglycerate levels) will produce heat intracellularly to raise the temperature of the cell between the 8.0° Centigrade and the 9.5° Centigrade range. Thus, even if all of the cells were to possess an equal concentration of the particles, the application of the chemical heating would produce a similar rise in temperature in all cells, which within the range desired, would do no harm to the normal cells while killing the cancer cells. There does not appear to be any danger in an increased concentration of the particles in the normal cells in view of the phagocytic characteristics of the cancer cells, but to efficiently use all of the minute particles and to permit the smallest dosage possible, it is desirable to utilize where beneficial a selective cancer cell seeking agent such as the radioisotopes or the antibodies. In this manner, an even greater concentration of the minute particles should be found in the cancer cells and a very minor amount, if not an exclusion of such particles, in the normal cells.

A specific example of the use of a radioisotope in accordance with the present invention is as follows:

EXAMPLE II

Gallium citrate—gallium-67 is incorporated into a sterilized isotonic 5% saline solution, the concentration being 1 millicurie of gallium-67 per cc. of the total composition. The amount to be injected could vary between 0.02 millicuries up to 0.1 millicuries per kg. of body weight. Upon injection, a 12-hour period is allotted for the gallium to isolate itself and selectively concentrate within the cancerous cells. Thereafter, the same hyperbaric oxygen chamber is applied in exactly the same manner as previously described in Example I. The amount of intracellular temperature increase is above 8.0° Centigrade and below 9.5° Centigrade and produces selective killing of the cancer cells without harming the normal cells.

When the gallium-67 is to be utilized as a cancer cell seeking agent, it may be bound to the particle in accordance with the manner in which iodine-131 has been bound to albumin. This combined gallium particle may be injected into the patient in precisely the same manner and it would be found that the gallium selectively delivers the particles to the cancer cells. Thereafter, when the cancer cell is subjected to the increased oxygen supply resulting from the hyperbaric oxygen chamber, the intracellular temperature of the cancer cell is increased 8.0° Centigrade to selectively destroy the cancer cell.

It is also possible that the known utility of the tumor specific cancer agents such as the chemotherapeutic agents, the radioisotopes or tumor specific cancer antibodies may be utilized in accordance with the present invention. For example, chemotherapeutic agents include 5-flurouracil, nitrogen mustard, actinomycin D, methotrexate, cytoxon and vincristine amongst a number of other agents known for similar utility. It is an aspect of the present invention that such known chemotherapeutic agents in a size less than 1 micron may be coated with an iron dextran material to produce a total particle of a size less than the approximate 1 micron particle size. The particles in effect encapsulate the chemotherapeutic agent and form a microsphere around the chemotherapeutic agent. The coating thickness of the minute particle should be approximately 0.1 micron. Thus, the size of the chemotherapeutic agent particle should be about 0.1 micron or less in order to bring about the total particle size of not greater than 1 micron and preferably less.

EXAMPLE III

The following is an example of the method of coating 5-flurouracil with iron dextran complex material: 5-flurouracil, a known acknowledged effective chemotherapeutic agent against cancer, is taken in its solid state and pulverized into particles 0.5 micron in size. These particles, in turn, are then coated with ferric hydroxide approximately 0.1 micron in thickness, in accordance with any of the conventional methods of coating submicron particles as described in U.S. Pat. No. 3,294,686.

These particles are then colloidally suspended in a 6% by weight aqueous dextran solution. This solution is introduced intravenously to the patient with the result that due to the phagocytic characteristics of the cancer cells, most of these particles will be deposited in the cytoplasm inside the cancer cells. This would take place about 4 to 8 hours after the intravenous injection. After the particles' deposition into the cytoplasm, the ferric hydroxide is acted upon by the cytoplasm and is converted to an organic iron complex (ferritin) which is then absorbed.

After approximately 24 hours, the ferric hydroxide coating is thus solubilized and the chemotherapeutic agent 5-flurouracil is released within the cancer cell where it can effectively kill the cell. Time is not critical, and may vary from 1 to 48 hours or more. The other tumor specific cancer agents may be similarly utilized.

EXAMPLE IV

The chemotherapeutic agent as encapsulated or integrated with an iron dextran material is described in EXAMPLE III, may be injected in precisely the same manner and when subjected to an increased oxygen supply resulting from the application of the hyperbaric oxygen chamber, will solubilize the iron dextran material due to its metabolism or oxidation and release the chemotherapeutic agent into the cancer cell. This intracellular release of the chemotherapeutic agent within the cancer cell under increased temperature would stimulate its efficacy against the cancer cells. The same example may be applied in the same manner to other tumor specific cancer agents.

EXAMPLE V

The encapsulating material may also be integrated with a low melting solid such as wax having a melting point higher than the resting temperature of the cells but below the death temperature of the normal cells. This temperature range may be therefore about 37.° and 46.5° Centigrade. This integrated material supplied as in Example III and encapsulating the chemotherapeutic agent after being absorbed in the cell and subjected to the increased metabolism or oxidation due to the increase in the oxygenation of the blood resulting from exposure to the hyperbaric oxygen chamber and by elevating serum 2,3-Diphosphoglycerate would result in an intracellular temperature increase which would melt the low melting point material and release the chemotherapeutic agent within the cancer cell. Similarly, the other tumor specific cancer agents may be similarly utilized.

As previously stated, a cancer cell seeking agent such as the radioisotope or antibodies may be utilized to more selectively direct the microsphere containing the chemotherapeutic agent to the particular cancer cell. As is known, chemotherapeutic agents sometimes have adverse side effects upon normal cells, but the present procedure would selectively release the chemotherapeutic agent intracellularly and selectively. Compared to the presence of the chemotherapeutic agent in the cancerous cell, the concentration of the chemotherapeutic agent in the normal cell would be minimal. The undesirable side effects upon the normal cells should therefore be greatly minimized if not totally avoided.

A further embodiment of the present invention which typifies the broad nature of the invention is the incorporation of any tumor specific cancer antibody or cancer treating radioisotope within the encapsulating microsphere in the manner previously described in Example III. Thereafter the antibody or radioactive isotope so coated may be introduced within the cell walls of the cancer cell and a hyperbaric oxygen chamber applied as in Example IV to cause the microspheres of the iron dextran material to release the antibody or the radioisotope intracellularly. It is also possible that the release of the encapsulated material may be solubilizing the spheres within the cell, as previously described in Example III.

One of the important features of the present invention is that there is destruction of the cancerous cells wherever they are located in the patient. Cells that may have become detached from the tumor and drift in the vascular system or lymphatic system would be killed by the present process.

EXAMPLE VI

As a specific example of the simplest form of the present invention, C15 platinum (or Bleomycin), a known and acknowledged effective chemotherapeutic agent against cancer, is taken and pulverized into particles 0.5 micron in size. These particles in turn are then coated with ferric hydroxide approximately 0.1 micron in thickness in accordance with any of the conventional methods of coating submicron particles as described in U.S. Pat. No. 3,294,686.

These particles are then colloidally suspended in a 6% by weight aqueous dextran solution. The solution is introduced intravenously to the patient with the result that, due to the phagocytic characteristics of the cancer cells, most of these particles will be deposited in the cytoplasm in the cancer cells. This will take place 8-24 hours after the intravenous injection. After the particles' deposition in the cytoplasm, a second particle system of an oxidizing agent is added which is then deposited in the cytoplasm within 6-8 hours. The combination of these agents releases the C15 platinum (Bleomycin) in the cell specifically in the tumor cells.

In addition, the FeOOH coating may be combined with a tumor specific antibody to enhance delivery to the tumor cells. Interaction with enzymes in the cytoplasm may also aid the process.

EXAMPLE VII

As a specific example of the simplest form of the present invention, iron oxyhydroxide particles of 0.7 micron size are suspended in a 5% dextrose aqueous solution in an amount of about 50 mg. of the particles per cc. Dosages in the amount of 30 mg. per kg. of body weight each of the particles should be made twice, by intravenous injections, each being 24 hours apart. The particles attain an intracellular localization in 8-20 hours. The oxidizing agent is then introduced and is deposited in the cytoplasm in 6-10 hours. The resultant intracellular chemical reaction generates heat and accomplishes an increase in intracellular temperature to selectively destroy the cancer cells.

This may also be utilized to enhance the efficacy of a chemotherapeutic agent i.e. C15 platinum (Bleomycin). A cancer cell seeking agent such as an antibody or radioisotope may be used to help direct either or both particle systems.

The addition of a cancer cell seeking agent such as radioisotopes or a tumor specific antibody is useful in directing the minute particles more selectively to the cancer cells. It is known that both radioisotopes and tumor specific antibodies have an affinity for the cancer cells and it is for this reason that the radioisotopes and antibodies have been found to have some application in the treatment of certain tumors. It is also possible that the radioisotopes may be used to substitute for the minute particles and be injected intravenously so as to be selectively taken up by the cancerous cells. Many of these radioisotopes, whether chemically or physically combined with other particles or used alone, are capable of metabolism or oxidation and with an increased supply of oxygen would react so as to generate heat intracellularly and thus raise the temperature of the cancer cells to the destructive temperature. Typical examples of useful radioisotopes are gallium-67, indium-113m, technetium-99m, fluorine, selenium-75. A great many other radioisotopes are useful and the above are only examples. The size and concentration of the radioisotopes alone or attached to the minute particles and the manner of injection is precisely the same as previously described.

These radioisotopes or antibodies may be bound to the particles as iodine-131 (the radioisotopes) has been bound to albumin for lung scanning in the past. Antibodies, for instance, may be attached to the iron dextran or other minute particles by use of an intermediate reducing glucose unit or its derivative such as metasaccharinic acid, in a conventional manner and as described in Example III, much as high molecular weight dextran is bound to ferric hydroxide.

It is known that antibodies can be formed by injection of cancer cells removed from one patient with cancer and injected into another patient. The injection of the cancer cells will in turn form antibodies in the substitute host as a defense against the foreign tumor cells from the original donor. These antibodies can be then selectively and in the past have been used to treat selected specific tumors. These antibodies have usefulness in the present invention as a selective cancer cell seeking agent.

These antibodies may be bound chemically or physically to the minute particles and then re-injected into the patient to be treated. Due to the antibodies' specificity for the original tumor cells, the antibodies bound to the particles will even more selectively induce the particles to be phagocytized by the cancer cells.

Antibodies with radioactive isotopes may be produced by feeding labeled amino acids to the animals producing the antibodies. This labeled amino acid is then incorporated into the antibody.

Large chemical entities can be attached to antibody molecules. Large proteins may be attached via diagotized atoxyl (p-amino-benzene arsenic acid). Antibodies may be bound while they are attached to a hapten or to an antigen. This protects the immunologically specific site of the antibody during the binding procedure.

There are many variations of the invention as described and this invention should be limited solely by the scope of the following claims.

I claim:

1. A process for the treatment of cancer cells in living tissue of a patient comprising the following steps:

introducing into the living tissue of the patient minute particles of a size not greater than one micron and capable of being metabolized by the cancer cells and capable of an increased rate of metabolism or oxidation by the increased availability of oxygen, absorbing said minute particles intracellularly into the cancer cells, thereafter, increasing the oxygen level of the blood of the patient, and thereby increasing the rate of intracellular chemical reaction in the cancer cells due at least in part to the intracellular presence of said minute particles, and generating intracellular heat therein, and continuing said increasing the oxygen level step until the intracellular temperature has increased at least 8.0 degrees Centigrade but not more than 9.5 degrees Centigrade to selectively induce thermal death of the cancer cells.

2. The process of claim 1 including,
said increasing the oxygen level step including subjecting the patient to hyperbaric air.

3. The process of claim 1 including,
said increasing the oxygen level step including subjecting the patient to hyperbaric oxygen.

4. The process of claim 1 including,
said increasing the oxygen level step including increasing the levels of 2,3-Diphosphoglycerate in the body to enhance the availability of the oxygen to the cells and thereby increasing the metabolism in the cells.

5. The process of claim 1 including,
said increasing the oxygen level step including introducing phosphates into the patient to increase the availability of oxygen to the cells and thereby increasing intracellular metabolism.

6. The process of claim 5 including,
said increasing the oxygen level step including subjecting the patient to hyperbaric oxygen.

7. The process of claim 1 including,
said minute particles comprising a compound which can be further oxidized.

8. The process of claim 7 including,
said compound being ferric oxyhydroxide, ferric hydroxide, iron carbonate, or iron citrate.

9. The process of claim 1 including,
said introducing step including intravenously injecting into the patient said minute particles.

10. The process of claim 1 including,
said introducing step including intravenously injecting into the patient said minute particles suspended in a liquid vehicle.

11. The process of claim 10 including,
said minute particles being integrated with a sugar molecule.

12. the process of claim 11 including,
said sugar molecule being dextrose, dextran, glucose or sucrose.

13. The process of claim 1 including,
said minute particles being bound to radioisotopes.

14. The process of claim 1 including,
said minute particles being bound to cancer antibodies.

15. The process of claim 1 including,
said minute particles comprising minute encapsulated chemotherapeutic agent particles.

16. The process of claim 1 including,
said minute particles comprising minute integrated chemotherapeutic agent particles.

17. The process of claim 1 including,
said minute particles comprising radioisotopes, and
said absorbing step including said radioisotopes being absorbed selectively in said cancer cells.

18. The process of claim 17 including,
said radioisotopes being gallium-67, indium-113m, technetium-99m, fluorine, or selenium-75.

19. The process of claim 1 including,
said introducing step including introducing a cancer cell seeking agent in a concentration sufficient to combine with and selectively direct said minute particles to the cancer cells.

20. The process of claim 19 including,
said cancer cell seeking agent being a radioisotope.

21. The process of claim 20 including,
said radioisotope being gallium-67, indium-113m, technetium-99m, fluorine or selenium-75.

22. The process of claim 19 including,
said cancer cell seeking agent being a tumor specific cancer antibody.

23. The process of claim 1 including,
said minute particles including a chemotherapeutic agent specific for treating cancer and a coating around said chemotherapeutic agent.

24. The process of claim 23 including,
said chemotherapeutic agent being 5-flurouracil, nitrogen mustard, actinomycin-D, methotrexate, cytoxan, or vincristine.

25. The process of claim 23 including,
removing said coating from said chemotherapeutic agent, after said absorbing step.

26. The process of claim 15 including,
said removing step including subjecting said minute particles to an increased oxygen supply.

27. The process of claim 23 including,
said increasing the oxygen level step including removing said coating from said chemotherapeutic agent, after said absorbing step.

28. A process for the treatment of cancer cells in living tissue of a patient comprising the following steps:

introducing into the living tissue of the patient minute particles of a total size not greater than one micron, capable of metabolizing and of reacting with another chemical, and having a chemotherapeutic agent and an agent coating solubilizable after a period of time by the cytoplasm of the cancer cell, depositing said minute particles intracellularly into the cancer cells, after said introducing step, and at least said period of time after said depositing step, solubilizing said coating and absorbing said chemotherapeutic agent in the cancer cells resulting in their death.

29. The process of claim 28 including,
said chemotherapeutic agent being nitrogen mustard, antinomycin D, methotrexate, 5-flurouracil, cytoxan, or vincristine, and
said coating comprising an iron dextran complex material.

30. The process of claim 29 including,
after said depositing step before said period of time has passed, subjecting said minute particles to an increased oxygen supply to remove said coating.

* * * * *